(12) United States Patent
Harper (10) Patent No.: US 8,940,032 B2
(45) Date of Patent: Jan. 27, 2015

(54) CONNECTION ASSEMBLY

(75) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 576 days.

(21) Appl. No.: 13/281,842

(22) Filed: Oct. 26, 2011

(65) Prior Publication Data

US 2013/0110182 A1    May 2, 2013

(51) Int. Cl.
*A61B 17/84* (2006.01)
*A61B 17/70* (2006.01)

(52) U.S. Cl.
CPC .................................. *A61B 17/7041* (2013.01)
USPC ............................. 606/328; 606/278; 606/279

(58) Field of Classification Search
USPC ............. 606/278, 297, 300, 324, 328, 60, 66, 606/246–247, 250–253, 277
See application file for complete search history.

(56) References Cited

U.S. PATENT DOCUMENTS

| | | | |
|---|---|---|---|
| 5,643,263 A | 7/1997 | Simonson | |
| 5,885,285 A | 3/1999 | Simonson | |
| 5,947,967 A | 9/1999 | Baker | |
| 6,183,473 B1 | 2/2001 | Ashman | |
| 6,471,703 B1 | 10/2002 | Ashman | |
| 6,520,962 B1 | 2/2003 | Taylor | |
| 6,562,038 B1 | 5/2003 | Morrison | |
| 7,261,715 B2 | 8/2007 | Rezach | |
| 7,377,922 B2 | 5/2008 | Baker | |
| 7,575,587 B2 | 8/2009 | Rezach | |
| 8,066,746 B2 * | 11/2011 | Glerum et al. | 606/278 |
| 8,070,781 B2 * | 12/2011 | Harper | 606/264 |
| 8,529,605 B2 * | 9/2013 | Glerum et al. | 606/278 |
| 2003/0176862 A1 | 9/2003 | Taylor | |
| 2004/0092930 A1 | 5/2004 | Petit | |
| 2004/0147928 A1 | 7/2004 | Landry | |
| 2005/0234450 A1 | 10/2005 | Barker | |
| 2006/0195096 A1 * | 8/2006 | Lee et al. | 606/61 |
| 2007/0156142 A1 | 7/2007 | Rezach | |
| 2007/0162008 A1 | 7/2007 | Cline, Jr. | |
| 2007/0173833 A1 | 7/2007 | Butler | |
| 2007/0238335 A1 | 10/2007 | Veldman | |
| 2007/0270810 A1 | 11/2007 | Sanders | |
| 2007/0293861 A1 | 12/2007 | Rezach | |
| 2008/0195122 A1 | 8/2008 | Castellvi | |
| 2009/0076549 A1 | 3/2009 | Lim | |
| 2009/0234391 A1 | 9/2009 | Butler | |
| 2010/0160971 A1 * | 6/2010 | Glerum et al. | 606/278 |

* cited by examiner

*Primary Examiner* — Todd Manahan
*Assistant Examiner* — Marcela I Shirsat (57) ABSTRACT

An orthopedic connection assembly is described that comprises a housing member for receiving an implant that is operably connected to a receiving member for receiving an anchor member. The connection assembly is configured to have a locking mechanism that secures and fixes the relative orientation between the implant and the anchor member. The connection assembly can comprise a plate member receivable within the housing member. When a securing member such as a set screw is introduced downwardly into the housing member to secure the implant, the securing member applies a lateral force to the plate member, which presses against an interference member within the receiving member. The interference member presses against the anchor member, such that the anchor member is fixed in a position relative to the implant.

20 Claims, 11 Drawing Sheets

CONNECTION ASSEMBLY

FIELD OF THE INVENTION

The present invention relates generally to a connection assembly, and more particularly, to a variable angle spinal implant connection assembly.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one of more of the components of the spine and the bone anchors are attached to the spinal components at one end and secured to the elongated rod at the other end.

However, due to the anatomical structure of the patient, the spinal condition being treated, and, in some cases, surgeon preference, the bone anchors may be required to be positioned at various angles and distances from the elongated rod. As a result, it can be difficult to obtain a secure connection between the elongated rod and the bone anchors.

As such, there exists a need for a connection assembly that is able to securely connect an elongated rod to bone anchors despite a variance in the angle and position of the bone anchors with respect to the rod.

SUMMARY OF THE INVENTION

Various embodiments of orthopedic connection assemblies are described herein. In some embodiments, an orthopedic connection assembly comprises a housing member including a first aperture for receiving a securing member and a second aperture for receiving a rod implant; a plate member insertable into the housing member through a third aperture; an interference member capable of engagement by the plate member; a receiving member for receiving the interference member therein, the receiving member including a receiving aperture for receiving an anchor member therethrough; and a cap member receivable over the receiving member, the cap member having an extension portion that is mateable with the housing member, wherein the orientations of the rod implant and the anchor member are fixed relative to each other by downwardly inserting the securing member into the housing member.

In some embodiments, an orthopedic connection assembly comprises a housing member for receiving an implant; a plate member receivable within the housing member; an interference member in contact with the plate member; and a receiving member for receiving an anchor member, wherein the receiving member is capable of operable connection with the housing member.

In some embodiments, an orthopedic connection assembly comprises a housing member for receiving an implant and a securing member; a plate member receivable in the housing member; and a receiving member for receiving an anchor member, wherein downward insertion of the securing member into contact with the plate member secures the orientation of the implant relative to the anchor member.

BRIEF DESCRIPTION OF THE DRAWINGS

The present invention will become more fully understood from the detailed description and the accompanying drawings, wherein.

DETAILED DESCRIPTION OF THE ILLUSTRATED EMBODIMENTS,

The following description of the preferred embodiment(s) is merely exemplary in nature and is in no way intended to limit the invention, its application, or uses.

With reference to FIGS. 1-4, a preferred embodiment of a connection assembly 10 is illustrated. The connection assembly 10 preferably includes a housing member 12 and a receiving member 14. The housing member 12 includes an elongated aperture 16 at a first end for receiving at least a portion of a spinal implant 20, such as a spinal rod, and the receiving member 14 includes an aperture 22 at a first end for receiving at least a portion of an anchor 24, such as a bone screw. One of ordinary skill in the art would recognize that although only a bone screw is shown, the aperture 22 of the receiving member 14 is capable of receiving any number of anchors including, but not limited to, other orthopedic screws, hooks, bolts, or other similar bone anchoring devices. The housing member 12 and the receiving member 14 are preferably rotatably connected to each other. The rotatable connection can be of any suitable design, including a threaded connection, a snap-fit, or a captured connection.

In a preferred embodiment, the housing member 12 also includes a second aperture 26 at the first end for receiving a securing member 28. The second aperture 26 extends from an outer surface of the housing member 12 toward the elongated aperture 16. In a preferred embodiment, the second aperture 26 is in fluid communication with the elongated aperture 16. At least a portion of the second aperture 26 is preferably threaded to receive the securing member 28, but the second aperture 26 can also be non-threaded.

Figure 2:
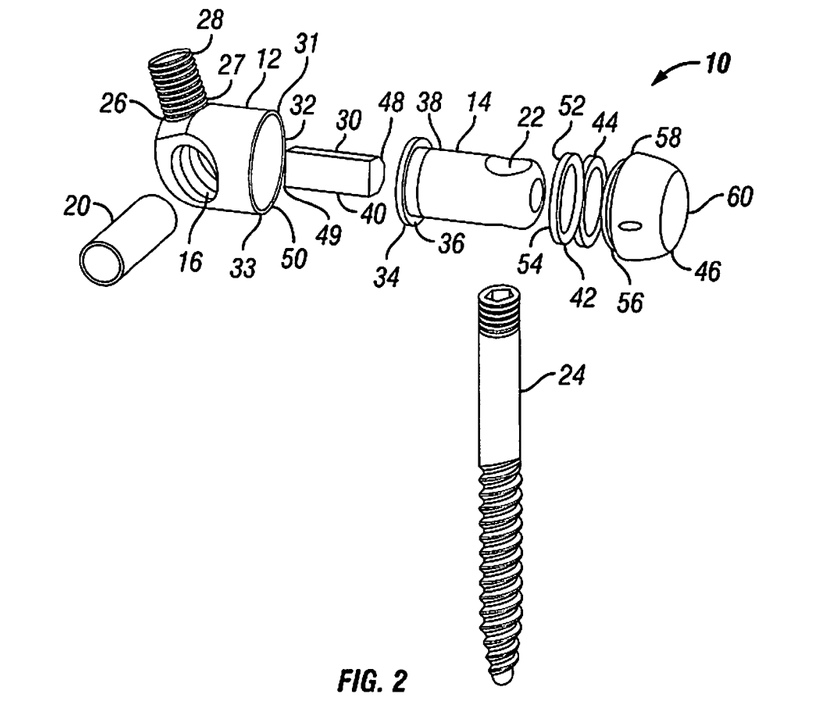
FIG. 2 is an exploded perspective view of the connection assembly shown in FIG. 1.

The securing member 28 is preferably a threaded set screw, as best seen in FIG. 2, but can be any type of securing member including, but not limited to, a bolt, a pin, a shoe, an interference member, or a cam member. In a preferred embodiment, the securing member 28 is captured in the second aperture 26 preventing accidental disengagement of the securing member 28 from the housing member 12. The securing member 28 is captured in the second aperture 26 by including an overhanging portion 29 on the securing member 28 that abuts against the termination of the threading in the second aperture 26.

With continued reference to FIG. 2, the housing member 12 also includes, in a preferred embodiment, a channel 30 which extends from a second end of the housing member 12 toward the first end of the housing member 12. The channel 30 is in fluid communication with the elongated opening 16. Preferably, at least a portion of the channel 30 includes threading 31 interrupted by at least one groove 32 extending from the second end of housing 12 toward the first end of housing member 12. In a preferred embodiment, the at least one groove 32 extends towards the first end of the housing member only a predetermined amount and preferably includes an end face 33 that defines the end of the groove 32.

Figure 5:
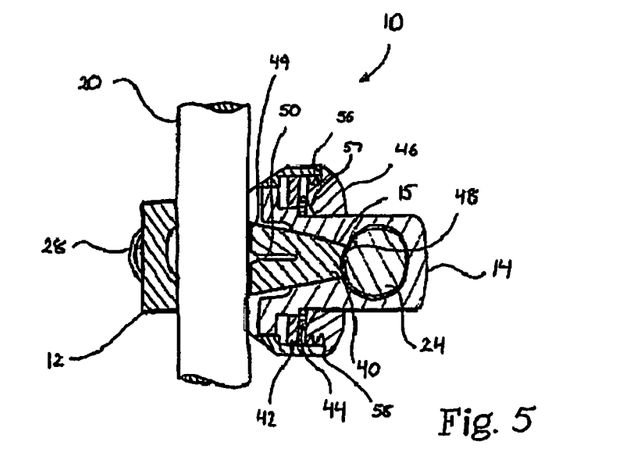
FIG. 5 is a cross-sectional view of the connection assembly shown in FIG. 1 in the direction of arrows B-B.

Referring to FIGS. 2 and 5, the receiving member 14, in a preferred embodiment, is generally cylindrical in shape with a generally tapered lumen 15. In another preferred embodiment, the lumen 15 may not be tapered and instead include a shoulder portion. The receiving member 14 further includes a radially outwardly extending rim portion 34 on a second end that has a plurality of ridges 36 preferably oriented toward the first end of the receiving member 14. In a preferred embodiment, the receiving member 14 also has a shoulder portion 38, spaced from the rim portion 34, on the second end of the receiving member 14. The receiving member 14 is configured and dimensioned to be received within the channel 30 of the housing member 12.

Turning back to FIGS. 1-5, the connection assembly 10 further includes, in a preferred embodiment, an interference member 40, a gear 42, a ring member 44, and a cap member 46. The interference member 40 has a generally polygonal shape that tapers from a second end to a first end. In a preferred embodiment, the first end of the interference member 40 has a saddle portion 48 that is configured and dimensioned to abut the anchor 24 and the second end of the interference portion 40 has a face 49 from which a cutout 50 extends towards the first end. The face 49 preferably is flat, but may also be arcuate and generally conforms to the shape of the spinal implant 20. In another preferred embodiment, the interference member 40 has a generally rectangular shape with a first end having a saddle portion that is configured and dimensioned to abut the anchor and a second end that flares outwardly and includes a face for abutting the spinal implant and a cutout. Although the cutout 50 is located near the second end of the interference portion 40, it is envisioned that the cutout 50 also be located near the first end of the interference portion 40. The interference portion 40 is configured and dimensioned to be received within the lumen 15 of the receiver member 14.

The gear 42, as best seen in FIG. 2, preferably is generally annular in shape and has a plurality of ridges 52 on one face and at least one projection 54 extending radially outwardly from the gear 42. In a preferred embodiment, the gear 42 is configured and dimensioned to fit over the shoulder portion 38 of the receiving member 14 and within channel 30 of the housing member 12. The gear 42 is preferably oriented so that the ridges 52 face the ridges 36 on the rim portion 34 of the receiving member 14 and the at least one projection 54 is received within the at least one groove 32 in the housing member 12.

Figure 4:
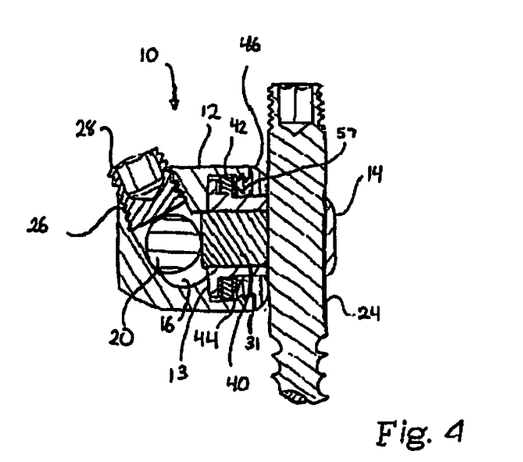
FIG. 4 is a cross-sectional view of the connection assembly shown in FIG. 1 in the direction of arrows A-A.

In a preferred embodiment, the ring member 44 is generally annular in shape, has a first face and a second face, and is configured and dimensioned to fit over the receiving member 14 and abut against the shoulder portion 38, as best seen in FIGS. 4 and 5. Preferably, the ring member 44 also is configured and dimensioned to be received within the channel 30 of the housing member 12. In a preferred embodiment, the ring member 44 is made from titanium, but the ring member 44 can also be made from any biocompatible material including resilient polymers.

The cap member 46, in a preferred embodiment, is generally cylindrical in shape and tapers from a first end to a second end. The cap member includes an extension portion 56 near the first end of the cap member and a lumen 60. As best seen in FIGS. 2, 4 and 5, the extension portion 56 preferably is threaded along at least a portion thereof and includes a ramp portion 57. Although the extension portion 56 preferably includes threading, in another preferred embodiment, the extension portion may not be threaded. Preferably, the diameter of the extension portion 56 is smaller than the diameter of the portion of the cap member 46 immediately adjacent to the extension portion 56 creating a shoulder portion 58. In a preferred embodiment, the cap member 46 is configured and dimensioned so the extension portion 56 engages the threading 31 in the channel 30 of the housing member 12 and the shoulder portion 58 abuts the second end of the housing member 12. The lumen 60 of the cap member 46 is configured and dimensioned to receive the receiving member 14. In a preferred embodiment, the cap member 46 is captured in the channel 30 of the housing member 12 to prevent the cap member 46 from inadvertently unthreading from the housing member 12.

With reference to FIGS. 1 and 3-5, in a preferred arrangement of the elements of the connection assembly 10, the housing member 12 is rotatably connected to the receiving member 14. As mentioned above, the receiving member 14 is received within the channel 30 of the housing member 12. In a preferred embodiment, the second end of the receiving member 14 abuts a medial wall 13 located within the housing member 12 and the first end of the receiving member 14 extends beyond the second end of the housing member 12. Positioned within the lumen 15 of the receiving member 14 is the interference member 40.

In a preferred embodiment, also received within the channel 30 of the housing member 12 is the gear 42 which fits over the shoulder portion 38 of the receiving member 14. The at least one projection 54 on the gear 42 is received within the at least one groove 32 and preferably abuts the end face 33 of the groove 32. The end face 33 of the groove 32 is spaced from the medial wall 13 of the housing member 12 by a predetermined amount, so the gear 42, when placed in the channel 30, is spaced from the rim portion 34 of the receiving member 14 by a predetermined amount. Accordingly, the ridges 36 on the rim portion 34 are spaced from the ridges 52 on the gear 42. The purpose of this spacing is important and is explained further below.

In a preferred embodiment, the ring member 44 is also received within the channel 30 of the housing member 12 and also fits over the receiving member 14. However, the inner diameter of the ring member 44 is smaller than the shoulder portion 38 of the receiving member 14. As a result, at least a portion of the second face of the ring member 44 will abut the shoulder portion 38. Preferably, the remaining portion of the second face of the ring member 44 will contact the gear 42.

The cap member 46, in a preferred embodiment, is also received within the channel 30 of the housing member 12 and also fits over the receiving member 14. The threads on the threaded potion 56 engage with the threads 31 on the channel 30 to threadingly engage the threaded cap 46. Preferably, the threaded portion 56 is threaded into the channel 30 until the shoulder portion 58 contacts the second end of the housing member 12. In this position, the ramp portion 57 of the threaded portion 56 abuts the first face of the ring member 44.

The preferred arrangement of the elements, as discussed above, allow the housing member 12, the gear 42 and the cap member 46 to rotate with respect to the receiving member 14, the ring member 44, and the interference member 40. As the housing member 12 rotates, the gear 42 will also rotate because of the at least one projection 54 located in the at least one groove 32. Likewise, since the cap member 46 is threaded and preferably captured in the channel 30 of the housing member 12, the cap member 46 also rotates when the housing member 12 rotates. In contrast, the receiving member 14, although captured within the channel 30 of the housing member 12 by virtue of the cap member 46 and the rim portion 34, is capable of rotating as well as translating within the channel 30. Accordingly, the receiving member 14 does not rotate when the housing member 12 rotates. Similarly, the ring member 44, although captured within the channel 30 of the housing member 12 by virtue of the shoulder portion 38 of the receiving member 14 and the ramp portion 57 of the cap member 46, is capable of rotating within channel 30. Consequently, the ring member 44 does not rotate when the housing member 12 rotates.

Figure 1:
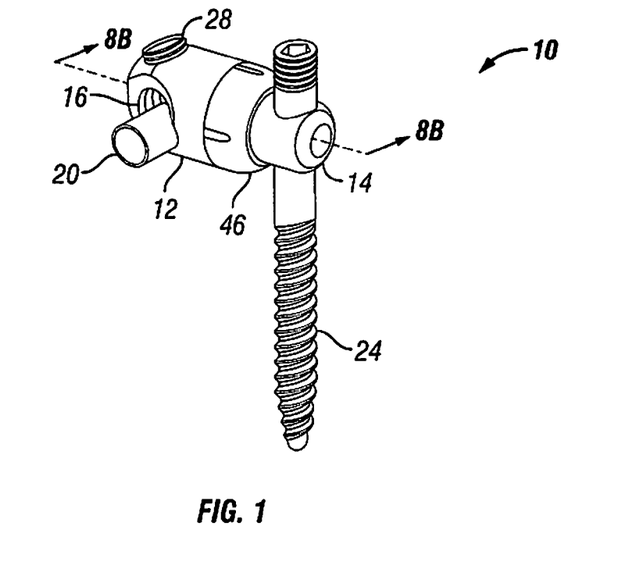
FIG. 1 is a perspective view of one embodiment of a connection assembly.
Figure 3:
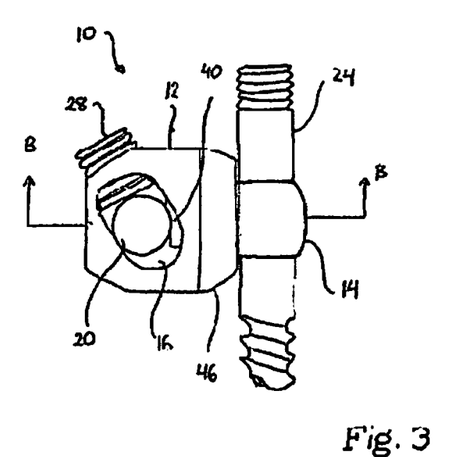
FIG. 3 is an elevated side view of the connection assembly shown in FIG. 1.

A preferred connection of the spinal implant 20 to the anchor 24 through the connection assembly 10 is best depicted in FIGS. 1, 3 and 4. In an exemplary use, the anchor 24 is implanted into a component of the spinal column, such as a vertebral body in the spinal column. Preferably, the aperture 22 of the receiving member 14 of the connection assembly 10 receives the anchor 24. The aperture 22 is configured and dimensioned to receive any portion of the anchor 24 allowing the connection assembly 10 to be placed anywhere along the length of the anchor 24. Accordingly, the connection assembly 10 can be translated along the anchor 24 until the desired position is achieved.

In an exemplary use, the spinal implant 20 is typically placed along at least a portion of the length of the spinal column in an orientation that is generally perpendicular to the anchor 24. Preferably, the spinal implant 20 is also received in the connection assembly 10, where the spinal implant 20 is received in the elongated opening 16 in the housing member 12. The elongated opening 16 is configured and dimensioned to receive any portion of the spinal implant 20 allowing the connection assembly 10 to be place anywhere along the length of the spinal implant 20.

Additionally, since the housing member 12 and the receiving member 14 are rotatably connected to each other, even if the anchor 24 and the spinal implant 20 are angularly offset, the connection member 10 can be oriented to a desired position to connect the spinal implant 20 and the anchor 24. Once the desired angular orientation and translational positioning of the connection assembly 10 with respect to the anchor 24 and the spinal implant 20 is achieved, the connection assembly 10 can be locked, securing the anchor 24 and the spinal implant 20.

To lock the connection assembly 10, the securing member 28 is threaded into the second aperture 26 in the housing member 12 where it contacts and pushes the spinal implant 20 toward the anchor 24. The spinal implant 20 contacts the face 49 of the interference member 40 and pushes the interference member 40 towards the anchor 24. As the interference member 40 is pushed by the spinal implant 20 towards the anchor 24, the interference member 40, with the aid of the cutout 50, compresses in the lumen 15 of the receiving member 14, and continues towards the anchor 24, while the receiving member 14 remains stationary. The saddle portion 48 of the interference member 40 abuts the anchor 24, pushing the anchor 24 into a sidewall of the aperture 22 in the receiving member 14, locking the anchor 24 in place with respect to the connector assembly 10.

As the spinal implant 20 continues to move towards the anchor 24 and continues to push the interference member 40, the interference member 40 no longer being able to compress any further in the lumen 15, pushes against the walls of the lumen 15 and moves the receiving member 14. As the receiving member 14 moves, the shoulder portion 38 pushes against the second face of the ring member 44. Since the first face of the ring member 44 abuts the ramp portion 57 of the cap member 46, after a predetermined force is applied to the ring member 44 by the shoulder portion 38, the ring member 44 deflects or bends in the direction of the ramp portion 57. With the ring member 44 no longer blocking the shoulder portion 38, the receiving member 14 continues moving towards the anchor 24 until the ridges 36 on the rim portion 34 of the receiving member 14 engage the ridges 52 on the gear 42. With the ridges 36 and 52 engaged, the relative rotation of the housing member 12 and the receiving member 14 of the connection assembly 10 is locked. At this point, the spinal implant 20 is also locked in place between the threaded member 28 and the walls of the housing member 12 that define the elongated opening 16. With the spinal implant 20 locked in place, the relative rotation of the housing member 12 and the receiving member 14 locked, and the anchor 24 locked in place, the entire assembly is locked against movement. Adjustments to the entire assembly can be made by loosening the threaded member 28 and then re-tightening the threaded member 28 once the preferred positioning and orientation has be achieved.

It is important to note that because of the shoulder portion 38 abutting the ring member 44 and the at least one projection 54 of the gear 42 abutting the end face 33 of the at least one groove 32, prior to the bending or deflection of the ring member 44, the ridges 36 on the rim portion 34 of the receiving member 14 can not engage the ridges 52 on the gear 42. This arrangement of elements prevents any inadvertent engagement of the ridges 36, 52 thereby preventing any unintended rotational locking of the housing member 12 with respect to the receiving member 14.

Figure 6:
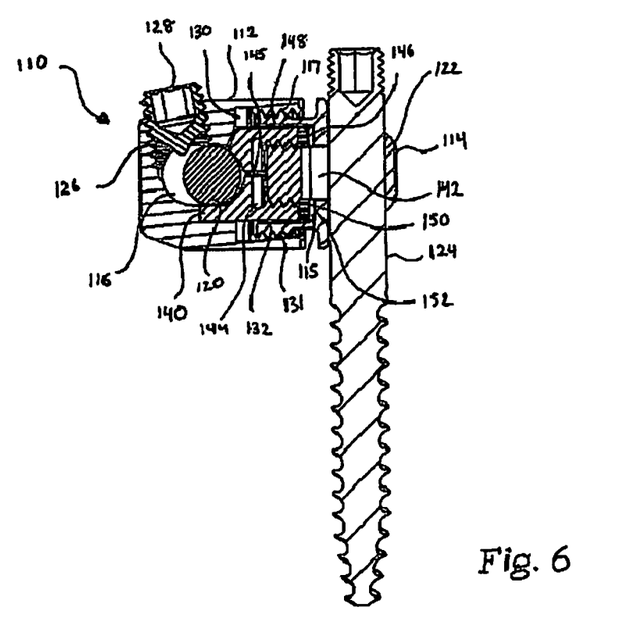
FIG. 6 is a cross-sectional view of another embodiment of a connection assembly.

Turning now to FIG. 6, a second preferred embodiment of a connection assembly 110 is shown. The connection assembly 110 preferably includes a housing member 112 and a receiving member 114. The housing member 112 includes an elongated aperture 116 at a first end for receiving at least a portion of a spinal implant 120 and the receiving member 114 includes an aperture 122 at a first end for receiving at least a portion of an anchor 124. The housing member 112 and the receiving member 114 are preferably rotatably connected to each other.

In a preferred embodiment, the housing member 112 also includes a second aperture 126 at the first end for receiving a securing member 128. The second aperture 126 extends from an outer surface of the housing member 112 toward the elongated aperture 116. In a preferred embodiment, the second aperture 126 is in fluid communication with the elongated aperture 116. At least a portion of the second aperture 126 is preferably threaded to receive the securing member 128. In a preferred embodiment, the securing member 128 is captured in the second aperture 126 preventing accidental disengagement of the securing member 128 from the housing member 112.

With continued reference to FIG. 6, the housing member 112 also includes, in a preferred embodiment, a channel 130 which extends from a second end of the housing member 112 toward the first end of the housing member 112. The channel 130 is in fluid communication with the elongated opening 116. Preferably, at least a portion of the channel 130 includes threading 131.

The receiving member 114, in a preferred embodiment, is generally cylindrical in shape with a cylindrical lumen 115 extending from a second end to the first end. Preferably, the cylindrical lumen is in fluid communication with the aperture 122. In a preferred embodiment, in the lumen 115 of the receiving member 114, a plurality of ridges 132 are present. The receiving member 114 is configured and dimensioned to be received within the channel 130 of the housing member 112 and includes threading 117 on an outer surface thereof to engage with the threading 131 in the channel 130. Since the receiving member 114 is threadingly received in the channel 130 of the housing member 112, the lateral position of the receiving member 114 with respect to the housing member 112 can be adjusted by rotating the receiving member 114. This allows for controlled lateral adjustment of the anchor 124 with respect to the spinal implant 120.

The connection assembly 110 further includes, in a preferred embodiment, an implant interference member 140 and an anchor interference member 142. The implant interference member 140 has a generally cylindrical shape and includes a channel 144 that extends from a first end towards a second end of the implant interference member 140. In a preferred embodiment, at least a portion of the channel 144 of the implant interference member 140 includes threading 146 to engage the anchor interference member 142. The implant interference member 140 also preferably includes at least one cutout portion 145, extending from the second end towards the first end, that separates at least a portion of the implant interference member 140 into sections. In a preferred embodiment, the implant interference member 140 also includes ridges 148 on an outer surface thereof. The implant interference member 140 is configured and dimensioned to be received in part within the lumen 115 of the receiving member 144 and in part within the channel 130 of the housing member 112.

The anchor interference member 142, in a preferred embodiment, also is generally cylindrical and includes threading 150 extending along at least a portion of the anchor interference member 142 from a second towards a first end. The anchor interference member 142 is configured and dimensioned to be received within the channel 144 of the implant interference member 144. In a preferred embodiment, the threading 150 of the anchor interference member 142 threadingly engages the threading 146 in the channel 144 of the implant interference member 140.

With continued reference to FIG. 6, to lock the connection assembly 110, the securing member 128 is threaded into the second aperture 126 in the housing member 112 where it contacts and pushes the spinal implant 120 toward the anchor 124. The spinal implant 120 contacts the implant interference member 140 and pushes the implant interference member 140 towards the anchor 124. As the implant interference member 140 is pushed by the spinal implant 120 towards the anchor 124, the anchor interference member 142, which is threadingly engaged with the implant interference member 140, also moves towards the anchor 124. The first end of the anchor interference member 142 abuts the anchor 124, pushing the anchor 124 into a sidewall of the aperture 122 in the receiving member 114, locking the anchor 124 in place with respect to the connector assembly 110.

As the spinal implant 120 continues to move towards the anchor 124 and continues to push the implant interference member 140, the implant interference member 140 abuts against a medial wall 152 in the receiving member 114 and is no longer able to translate in the lumen 115 of the receiving member 114. The continued movement of the spinal implant 120 toward the anchor 124 results in the implant interference member 140 splaying radially outwardly with the aid of the at least one cutout 145. The implant interference member 140 splays outwardly until until the ridges 148 on the outer surface of the implant interference member 140 engage the ridges 132 in the lumen 115 of the receiving member 114. With the ridges 132 and 148 engaged, the relative rotation of the housing member 112 and the receiving member 114 of the connection assembly 110 is locked. At this point, the spinal implant 120 is also locked in place between the threaded member 128 and the walls of the housing member 112 that define the elongated opening 116. With the spinal implant 120 locked in place, the relative rotation of the housing member 112 and the receiving member 114 locked, and the anchor 124 locked in place, the entire assembly is locked against movement. Adjustments to the entire assembly can be made by loosening the threaded member 128 and then re-tightening the threaded member 128 once the preferred positioning and orientation has be achieved.

Additional Embodiments of Connection Assemblies

Additional embodiments of improved connection assemblies for securely connecting a spinal implant to a bone anchor are discussed below. The connection assemblies advantageously rely on a low number of components, have a low profile and are easy to manufacture.

Figure 7:
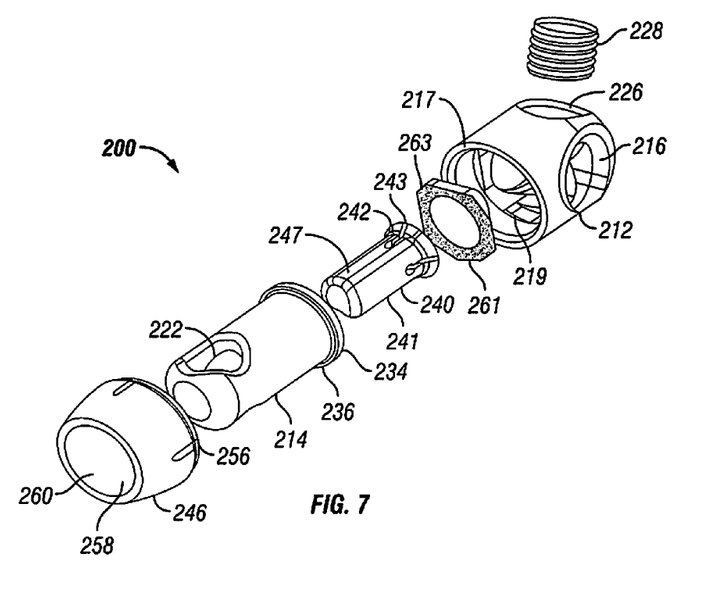
FIG. 7 is an exploded view of an alternative embodiment of a connection assembly.

FIG. 7 is an exploded view of an alternative embodiment of a connection assembly. The connection assembly 200 comprises a cap member 246, a receiving member 214, an interference member 240, a plate member 261, a housing member 212 and a securing member 228.

The housing member 212 of the connection assembly 200 comprises a first aperture 216 at a first end for receiving at least a portion of a spinal implant, such as a rod member. The housing member 212 further includes a second aperture 226 for receiving a securing member 228, such as a set screw. The securing member 228 is configured such that upon downward placement of the securing member 228, the securing member 228 will apply a lateral force on the plate member 261, which will then push against the interference member 240. A third aperture 219 opens from a second end of the housing member 212. The third aperture 219 is configured to receive the plate member 261 therein. The housing member 212 further includes a rim portion 217 that is configured to receive an extension portion of the cap member 246, as discussed further below.

Figure 12A:
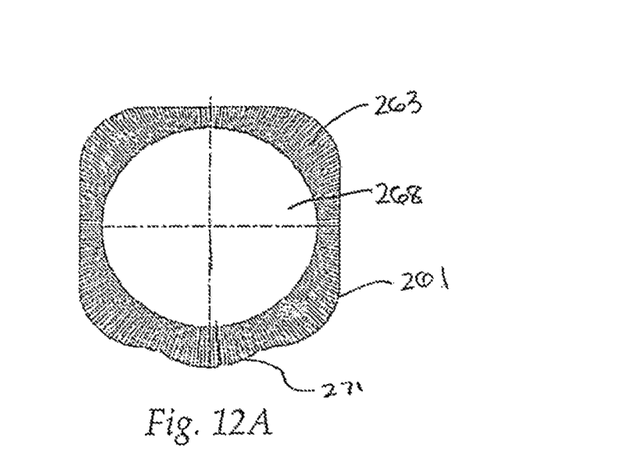
FIG. 12A is a top view of a plate member of the connection assembly in FIG. 7.
Figure 12B:
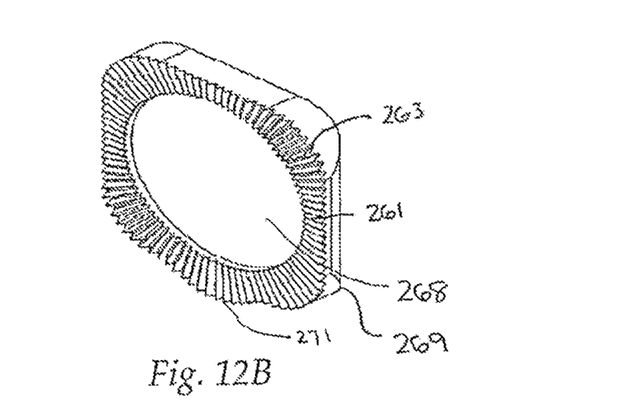
FIG. 12B is a top perspective view of a plate member of the connection assembly in FIG. 7.
Figure 12C:
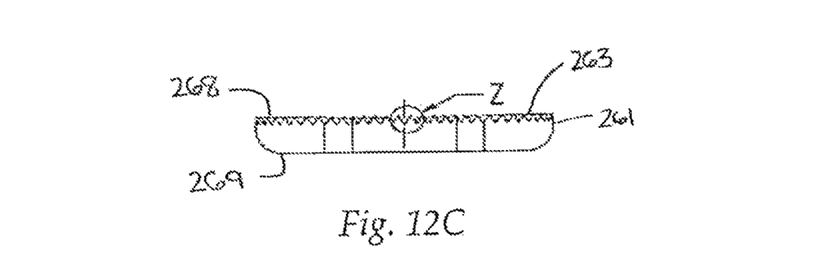
FIG. 12C is a side view of a plate member of the connection assembly in FIG. 7.

The plate member 261 comprises a first surface 268 including surface features 263 and a second surface 269 that is substantially smooth, as shown in FIGS. 12A-12C. In some embodiments, the surface features 263 on the first surface 268 can comprise teeth or ridges. The plate member 261 is configured to be received in the third aperture 219 of the housing member 212 such that its second surface 269 faces the interior of the housing member 212. As the set screw 228 is inserted downwardly through the second aperture 226 of the housing member 212, the set screw 228 will contact and abut the second surface 269 of plate member 261, which will abut and contact the interference member 240.

The interference member 240 comprises a body 240 affixed to a tapering rim member 242. While in some embodiments, the body 240 is cylindrical, in other embodiments, the body 240 has at least one or more flattened surfaces 247, as shown in FIG. 7. The flattened surfaces 247 advantageously serve as a guide such that the interference member 240 would fit in a specific orientation within the receiving member 214. The rim member 242 of the interference member 240 comprises a plurality of slits 243 that extend around the rim. The plurality of slits 243 advantageously provide some flexibility to the rim member 242 as the assembly is being securely assembled.

The interference member 240 is configured to be received within the receiving member 214. As the set screw 228 is downwardly inserted into the housing member 212 to apply a force against the plate member 261, the plate member 261 pushes against the interference member 240 adjacent to the rim member 242. The interference member 240 is then pushed further into the receiving member 214, whereby a distal end of the interference member 240 opposite from the rim member pushes against an anchor member (not shown) inserted into the receiving member aperture 222. The connection assembly 200 thereby provides a means to securely connect an implant (e.g., a rod member) through the housing 212 and an anchor member (e.g., a bone anchor) through the receiving member 214.

The receiving member 214 comprises an aperture 222 for receiving an anchor member that can be secured to bone. On an opposite end of the receiving member 214, the receiving member 214 further comprises a first end having a radially outwardly extending rim portion 34 that includes a plurality of ridges 36. On a surface of the receiving member 214 adjacent the rim portion 34, there are a plurality of surface features 223 (shown in FIGS. 14A and 14B) that contact, mesh, complement and/or engage with the surface features 263 of the plate member 261. The receiving member 214 further includes an inner lumen that is configured to receive the interference member 240 therethrough. The interference member 240 can push against the anchor member positioned in the aperture 222, thereby helping to create a secure system.

The cap member 246 comprises an opening 258 that leads to an inner lumen 260. The inner lumen 260 is configured to receive the receiving member 214. On an opposite end from the opening 258, the cap member 246 includes an extension portion 256. In some embodiments, at least a portion of the extension portion 256 is threaded. The extension portion 256 of the cap member 246 can be received within the rim portion 217 of the housing member 212 (as shown in FIG. 8B), thereby helping to form a secure assembly of low profile.

Figure 8A:
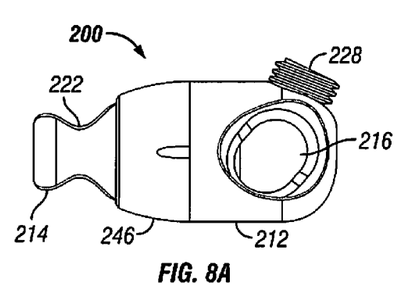
FIG. 8A is a side view of the connection assembly in FIG. 7.
Figure 8B:
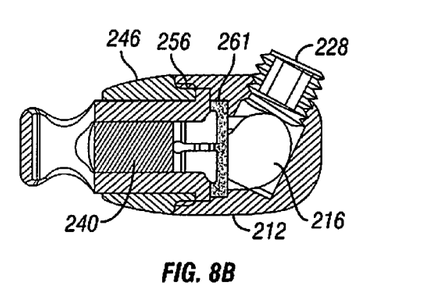
FIG. 8B is a side cross-sectional view of the connection assembly in FIG. 7.

The assembled components of the connection assembly are shown in FIGS. 8A and 8B. FIG. 8A is a side view of the connection assembly, while FIG. 8B is a side cross-sectional view of the connection assembly.

In the assembled configuration, the connection assembly operates as follows. A rod member (not shown) can be inserted through aperture 216 of housing member 212, while an anchor member (not shown) can be inserted through aperture 222 of receiving member 214. The rod member can be oriented in a number of variable angles relative to the anchor member prior to setting the securing member 228.

Once a desired orientation is achieved, the securing member 228 is downwardly threaded into the housing member 212. As the securing member 228 is downwardly threaded, it applies a lateral force on the plate member 261. The plate member 261 then presses against the interference member 240, which presses against the anchor member in the receiving member 214. Advantageously, the tabs formed by the slits 243 of the interference member 240 flex in as they travel along a conical ramp of the receiving member 214. In addition, the surface features 263 of the plate member 261 then press against the surface features 223 of the receiving member 214, thereby limiting axial rotation within the assembly. The improved connection assembly thus provides a convenient mechanism to secure an implant to an anchor member using a relatively small number of components. Furthermore, the connection assembly provides a one step locking mechanism via the downward insertion of the securing member 228.

Figure 9A:
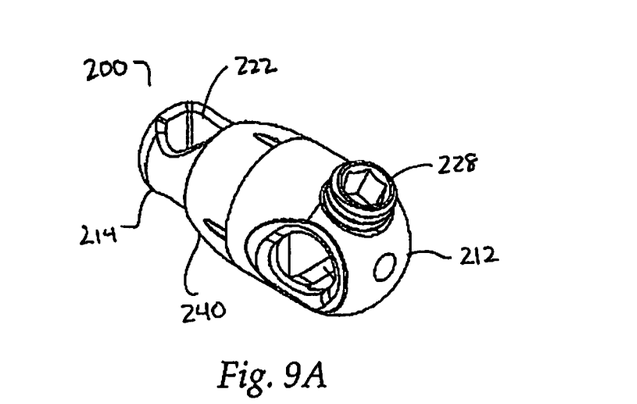
FIG. 9A is a top perspective view of the connection assembly in FIG. 7.
Figure 9B:
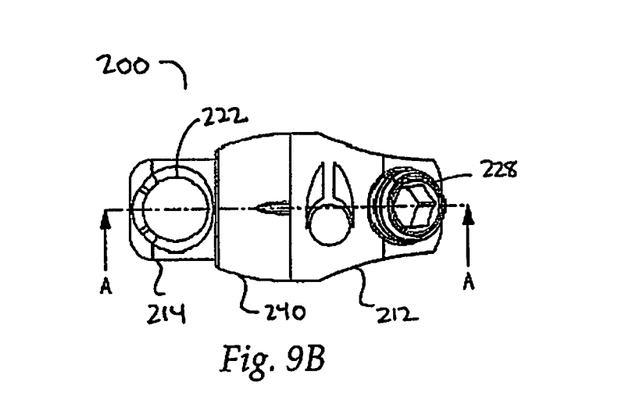
FIG. 9B is a top view of the connection assembly in FIG. 7.

FIGS. 9A and 9B illustrate different views of the connection assembly 200 in FIG. 7. From these views, one can see how the different components, including the housing member 212, receiving member 214, and cap member 240 are securely connected to one another.

Figure 10A:
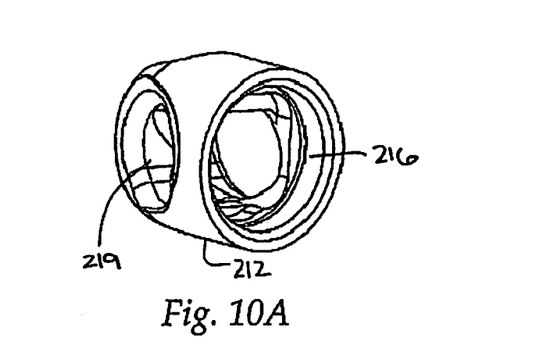
FIG. 10A is a side perspective view of a housing member of the connection assembly in FIG. 7.
Figure 10B:
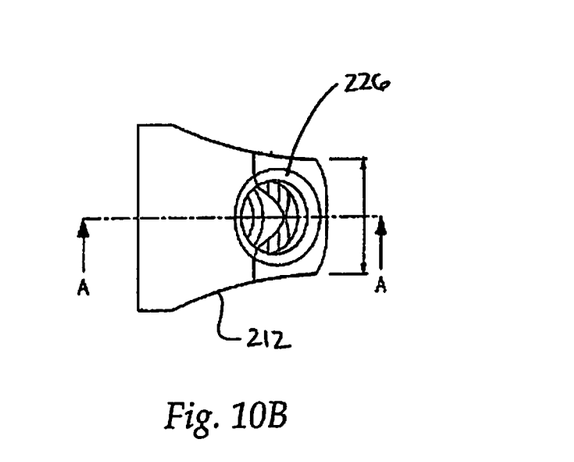
FIG. 10B is a top view of a housing member of the connection assembly in FIG. 7.

FIGS. 10A and 10B illustrate different views of a housing member of the connection assembly in FIG. 7. The housing member 212 is configured to include multiple apertures 216 and 219 for receiving an implant (e.g., a rod member) and plate member 261, respectively.

Figure 11A:
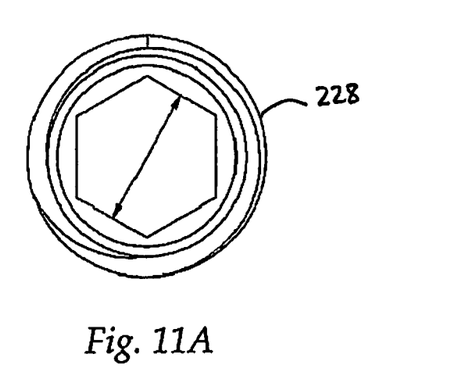
FIG. 11A is a top view of a securing member of the connection assembly in FIG. 7.
Figure 11B:
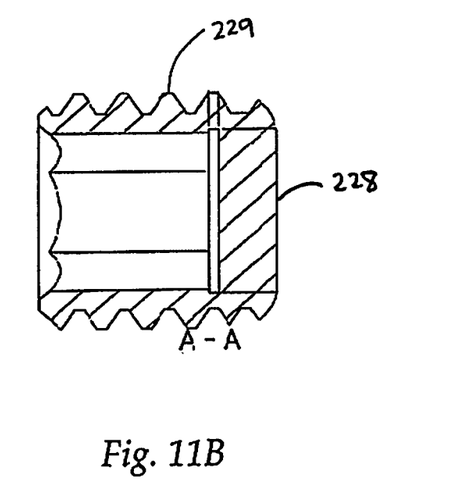
FIG. 11B is a side view of a securing member of the connection assembly in FIG. 7.

FIGS. 11A and 11B illustrate different views of a securing member 228. The securing member 228 can comprise a set screw having one or more threads 229, as shown in FIG. 11B.

FIGS. 12A-12C illustrate different views of a plate member 261. In some embodiments, the plate member 261 includes a first surface 268 that has a substantially smooth inner portion surrounded by surface features 263, as shown in FIG. 12A. In other embodiments, the plate member 261 can have surface features continuously on a surface 268. As shown in FIGS. 12A and 12B, in some embodiments, the plate member 261 can include one or more notches 271 such that the plate member is not entirely symmetrical across opposite edges. This lack of symmetry can advantageously serve as a guide in order to properly position the plate member 261 within the assembly.

Figure 13A:
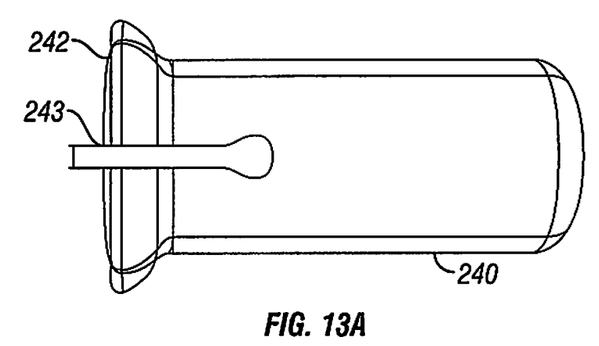
FIG. 13A is a side view of an interference member of the connection assembly in FIG. 7.
Figure 13B:
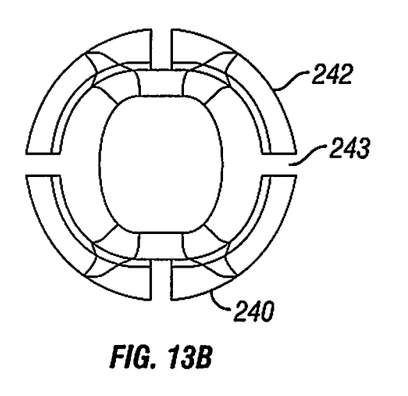
FIG. 13B is a top view of an interference member of the connection assembly in FIG. 7.

FIGS. 13A and 13B illustrate different views of an interference member 240 having a rim member 242 with a plurality of slits 243. While the interference member 240 is illustrated in FIG. 13B includes four slits 243 that are evenly distributed around the rim member, thereby providing for a substantially even distribution of forces, in other embodiments, the interference member 240 includes less or more than four slits that may or may not be evenly distributed.

Figure 14A:
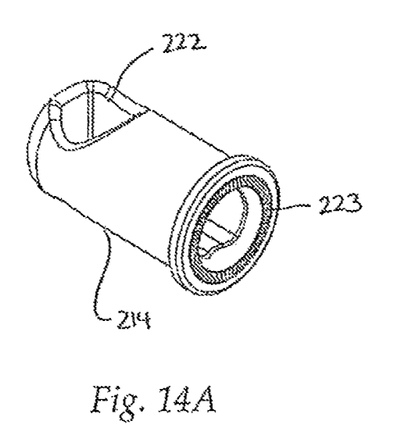
FIG. 14A is a top perspective view of a receiving member of the connection assembly in FIG. 7.
Figure 14B:
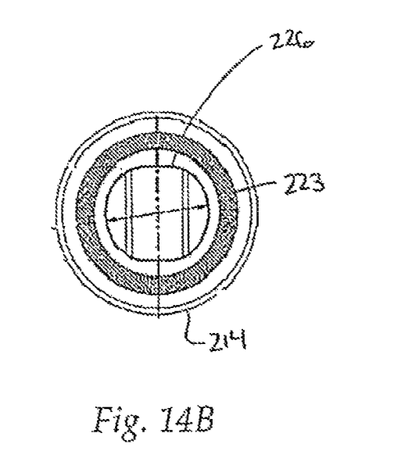
FIG. 14B is a top view of a receiving member of the connection assembly in FIG. 7.

FIGS. 14A and 14B illustrate different views of a receiving member 214. As shown in FIG. 14B, the receiving member 214 can include a lumen 226 that is configured to receive the interference member 240 therein. For example, the lumen 226 of the receiving member 214 can include flat side surfaces that can engage similar flat surfaces of an interference member 240 received therein.

Figure 15A:
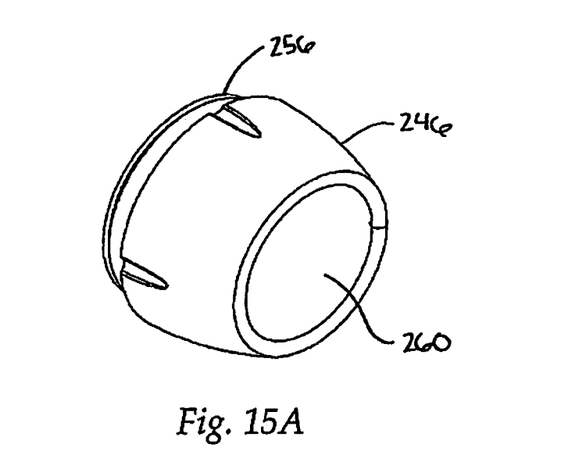
FIG. 15A is a top perspective view of a cap member of the connection assembly in FIG. 7.
Figure 15B:
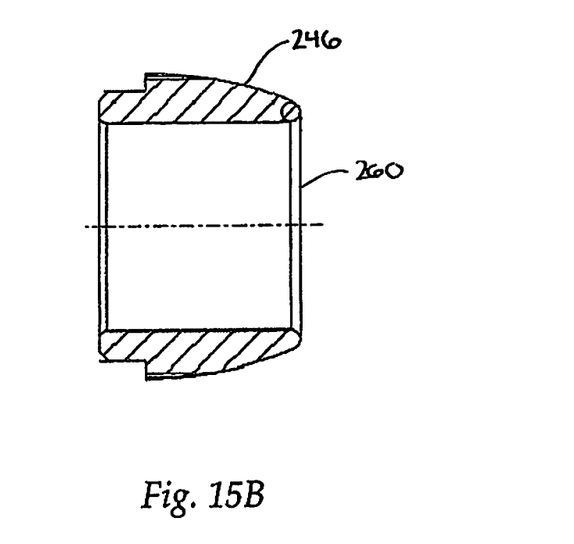
FIG. 15B is a side cross-sectional view of a cap member of the connection assembly in FIG. 7.

FIGS. 15A and 15B illustrate different views of a cap member 246. From these viewpoints, the body of the cap member, including its extension portion 256, is clearly illustrated.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orthopedic connection assembly comprising:
   a housing member including a first aperture for receiving a securing member and a second aperture for receiving a rod implant;
   a plate member insertable into the housing member through a third aperture;
   an interference member capable of engagement by the plate member;
   a receiving member for receiving the interference member therein, the receiving member including a receiving aperture for receiving an anchor member therethrough; and
   a cap member receivable over the receiving member, the cap member having an extension portion that is mateable with the housing member,
   wherein the orientations of the rod implant and the anchor member are fixed relative to each other by downwardly inserting the securing member into the housing member.

2. The assembly of claim 1, wherein the securing member comprises a set screw.

3. The assembly of claim 2, wherein the set screw includes a plurality of threads.

4. The assembly of claim 1, wherein the plate member includes a plurality of teeth.

5. The assembly of claim 4, wherein the receiving member includes a plurality of teeth that mesh with the teeth of the plate member.

6. The assembly of claim 1, wherein the extension portion of the cap member includes one or more grooves.

7. The assembly of claim 1, wherein the interference member includes one or more flat surfaces along its body.

8. The assembly of claim 1, wherein the downward insertion of the securing member into the housing member causes a lateral force to be applied to the plate member.

9. The assembly of claim 1, wherein the interference member comprises a body affixed to a tapering rim member.

10. The assembly of claim 9, wherein the body includes one or more flattened surfaces.

11. The assembly of claim 9, wherein tapering rim includes one or more slits that extend around the rim.

12. The assembly of claim 1, wherein the receiving member comprises a radially outward extending rim portion.

13. The assembly of claim 12, wherein a plurality of surface features are positioned adjacent the radially outward extending rim portion of the receiving member.

14. An orthopedic connection assembly comprising:
    a rod implant;
    an anchor implant;
    a housing member configured and dimensioned to receive the rod implant;
    a securing member receivable in the housing member:
    a plate member receivable within the housing member;
    an interference member in contact with the plate member; and
    a receiving member configured and dimensioned to receive the anchor member, wherein the receiving member is capable of operable connection with the housing member and
    wherein the interference member is received at least partially within the receiving member and
    wherein downward insertion of the securing member into contact with the rod implant moves the rod implant into contact with the plate member securing the orientation of the rod implant relative to the anchor member.

15. The assembly of claim 14, wherein the housing member includes an aperture for receiving a securing member.

16. The assembly of claim 15, wherein the plate member comprises surface features that encompass a smooth surface.

17. The assembly of claim 15, wherein the interference member comprises one or more slits that separate tab members.

18. The assembly of claim 17, wherein the slits are evenly distributed around the interference member.

19. The assembly of claim 15, wherein the interference member includes one or more flat surfaces.

20. The assembly of 19, wherein the inner lumen of the receiving member includes one or more flat surfaces that correspond to the flat surfaces of the interference member.

* * * * *